United States Patent [19]

Doyle

[11] Patent Number: 4,764,676
[45] Date of Patent: Aug. 16, 1988

[54] APPARATUS FOR SPECTRAL ANALYSIS OF CHROMATOGRAPHIC FRACTIONS

[75] Inventor: Walter M. Doyle, Laguna Beach, Calif.

[73] Assignee: Laser Precision Corporation, Irvine, Calif.

[21] Appl. No.: 921,212

[22] Filed: Oct. 20, 1986

[51] Int. Cl.$^4$ .............................................. G01J 3/42
[52] U.S. Cl. ................... 250/353; 250/339; 356/432
[58] Field of Search ............ 250/353, 341, 339, 358.1, 250/352; 356/432, 436, 440, 443, 51

[56] References Cited

U.S. PATENT DOCUMENTS

| | | | |
|---|---|---|---|
| 3,628,872 | 12/1971 | Miranda | 250/574 |
| 3,999,861 | 12/1976 | Bellinger | 356/246 |
| 4,129,781 | 12/1978 | Doyle | 250/341 |
| 4,222,670 | 9/1980 | Koshiishi | 356/440 |
| 4,473,295 | 9/1984 | Doyle | 356/73 |
| 4,594,533 | 6/1986 | Snook et al. | 356/440 |
| 4,661,706 | 4/1987 | Messerschmidt et al. | 250/353 |

Primary Examiner—Carolyn E. Fields
Assistant Examiner—John A. Miller
Attorney, Agent, or Firm—Thomas J. Plante

[57] ABSTRACT

An apparatus for spectral analysis of chemical fractions is disclosed in which separate samples are frozen on a substrate, and infrared radiation passes through the sample either before or after it is reflected from a surface on the other side of the substrate from the sample. This permits radiation to move toward and away from the sample at the same side of the sample, thus simplifying the sample-cooling and sample-deposition techniques. The optical system is designed to defocus (and thus avoid detection of) unwanted radiation reflected by the sample.

11 Claims, 4 Drawing Sheets

FIG. 1  Background

APPARATUS FOR SPECTRAL ANALYSIS OF CHROMATOGRAPHIC FRACTIONS

BACKGROUND OF THE INVENTION

This invention relates to the spectral analysis of small amounts of substances deposited on a substrate, which is maintained at a uniform low temperature (in an evacuated chamber). In particular, it concerns the use of infrared spectroscopy in the analysis of chromatographic fractions.

Chromatographic analysis is significantly improved by depositing (and freezing) the separated fractions on a substrate, and using infrared spectroscopy (FTIR) for sample analysis. In Reedy U.S. Pat. No. 4,158,772, issued June 19, 1979 various prior types of chromatographic analysis are discussed (Col. 1, lines 55–67), which "exhibit limited observation time and consequently suffer in both precision and resolution". The Reedy patent discloses a "matrix-isolation" technique, in which separated fractions are "entrapped within a frozen matrix of an inert substance such as argon or krypton gas".

The apparatus disclosed in the Reedy patent requires cooling the substrate to a very low temperature, e.g., the temperature provided by liquid helium. Maintenance of the required extremely low temperature requires very expensive apparatus.

A less costly apparatus for analysis of chromatographic fractions has been proposed in an article by Pentony, Shafer & Griffiths in the June, 1986 issue of the Journal of Chromatographic Science. They describe a system for analysis of chromatographic fractions, which involves depositing the fractions in a narrow track on a cooled transparent substrate, and then analyzing the deposited material by means of an infrared transmission microscope attached to an FTIR spectrometer. This system represents an advance over other means for the IR analysis of chromatographic fractions (whether gas, liquid, or supercritical fluid). However, it does have some drawbacks. In particular, the need to analyze the deposit in transmission (i.e., radiation entering on one side and exiting on the other) necessitates cooling the substrate from the edges. This tends to limit temperature uniformity, particularly at low temperatures such as liquid nitrogen temperature (77 degrees Kelvin). In addition, the need to focus the radiation to a small spot requires the use of optical elements quite close to the substrate, thus restricting the space available for cooling, for vacuum apparatus, and for the needed computer-controlled positioning devices.

It has been recognized that these space constraints could be relieved if the fractions could be deposited on a reflecting substrate and analyzed by means of reflectance microscopy. This would leave all the space on one side of the substrate free for cooling, and for the other required apparatus. However, experiments thus far have established that the spectra obtained in this way contained undesired artifacts, probably due to large spectral variations in the amount of radiation reflected from the surface of the deposited material. These variations are related to differences in its index of refraction (generally referred to as dispersion).

SUMMARY OF THE INVENTION

The present invention realizes the goal of placing all of the optics on one side of the substrate, while avoiding the spurious effects which can result when the first surface reflection from the deposited sample is viewed by the infrared detection apparatus. And it does this without requiring a solid argon or krypton matrix (with the attendant high equipment cost).

In any of the sample analysis techniques discussed, the illumination of the sample is accomplished by the transmission of radiation through each sample. The present invention uses a substrate which carries the deposited samples on one side (front), and which has a reflecting surface on the other side (back). The sample illumination is accomplished by the incident radiation either before or after that radiation has passed through the substrate and been reflected by the back of the substrate. This permits the illuminating radiation to enter and leave from the same side, providing significant practical advantages in the cooling and tracking (moving along a series of samples) structures.

Radiation reflected by the sample is spurious and if it reaches the detector, it will contain undesired artifacts. This problem is overcome in the present invention by "defocusing" this undesired radiation, so that very little of it reaches the detector. This is accomplished by an optical system in which the detector focal plane is imaged on the mirror image of the sample (instead of the sample) if the source is imaged on the sample, or in which the incident radiation is focused on the mirror image of the sample (instead of the sample) if the detector is imaged on the sample.

DETAILED DESCRIPTION OF SPECIFIC EMBODIMENTS

Figure 1:
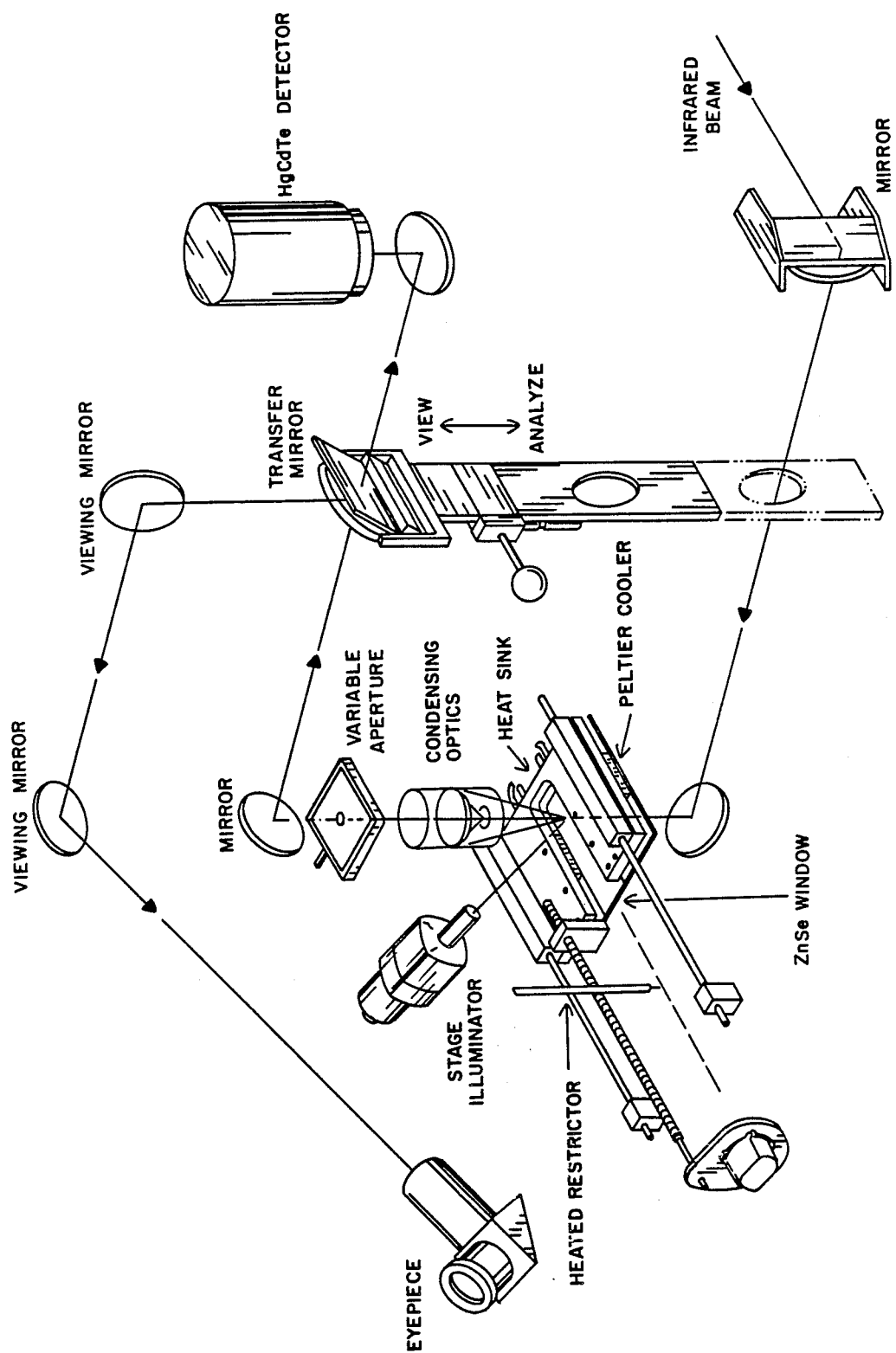
FIG. 1 is a copy of FIG. 1 of the Pentony et al article referred to above.

FIG. 1 is identical with FIG. 1 of the Pentony et al article mentioned above. The entering infrared beam is reflected upwardly through the sample, which is deposited on a transparent window. The reflected beam passes through the sample to the condensing optics, and thence through a variable aperture (or field stop). Additional mirrors direct the radiation to a cooled detector. Because it is desired to analyze many samples seriatim, the samples are deposited along the top of the window; and the window-supporting structure is caused to have reciprocating motion. Cooling of the sample is accomplished by a Peltier cooler, in which the window is mounted; and heat transmission must occur via the window, which is not an effective heat conductor.

Figure 2:
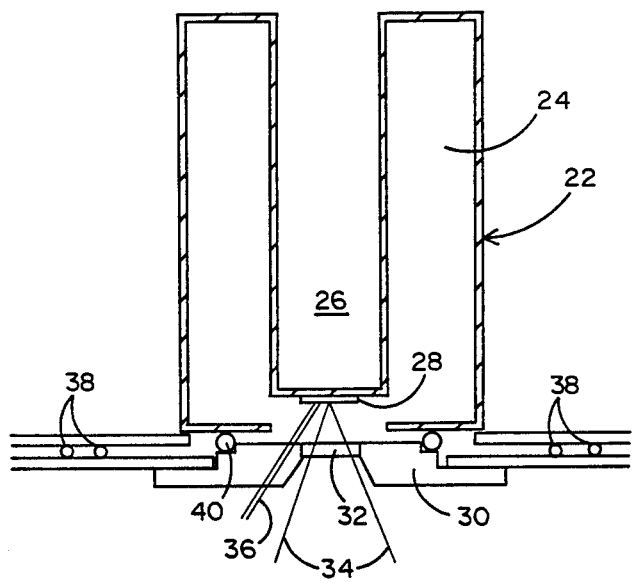
FIG. 2 is a cross-section showing, in the present invention, location of the sample inside a cooling device, with analytical radiation entering and exiting from the same side.

FIG. 2 illustrates, in a very general way, the cooling and structural advantages available if the sample illuminating radiation is reflected, i.e., enters and leaves the sample location from the same side. A movable Dewar 22 is shown having an evacuated chamber 24 surrounding a chamber 26 into which liquid nitrogen is poured. A sample-carrying substrate 28 is held against the lower wall of chamber 26. Because the side and bottom walls of chamber 26 are heat conducting, excellent cooling effect is provided on the entire upper surface of substrate 28. The cooling portion of the Dewar is designed to be mobile, with respect to a bottom-supporting plate 30, which has a transparent window 32 for entering and exiting radiation 34.

Mobility of the cooling unit, instead of the adjacent optical structure, is necessitated by the presence of a heated nozzle 36, which is used to deposit discreet samples on substrate 28, following a predetermined pattern, e.g., a spiral or zigzag pattern. The samples are deposited somewhat ahead of their optical illumination. As shown, roller bearings 38 may be used to permit low friction movement of the Dewar 22; and an O-ring seal 40 may be used to seal the vacuum chamber 24. The separated fractions, or samples, may be deposited, and subsequently illuminated, on the moving substrate 28 at a rate of approximately one per second. Thus, during a 30 minute run, about 1,800 samples would be analyzed.

The structure shown in FIG. 2 will be the subject of a separate patent application providing a detailed disclosure.

Figure 3:
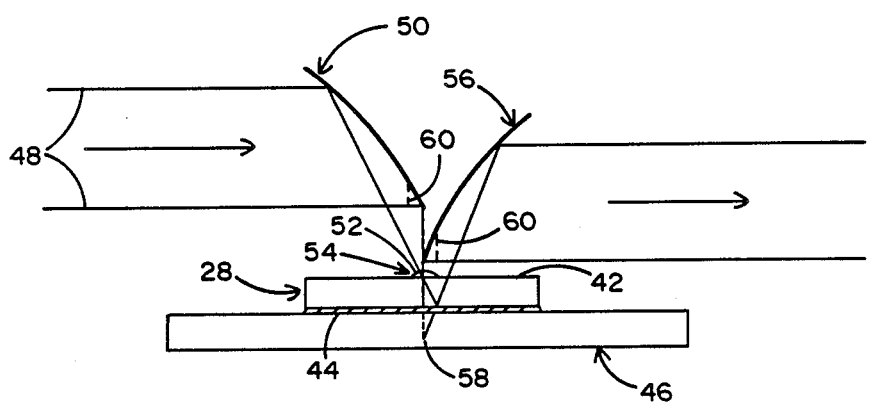
FIG. 3 is a schematic showing one embodiment of the present invention.

FIG. 3 shows an optical arrangement which uses reflectance as the means of illuminating the sample, while directing the analytical beam through the sample, and at the same time displacing (or defocusing) the spurious radiation which is reflected from the sample. In FIG. 3, a two mirror reflectance apparatus is used, which is a modification of the reflectance apparatus disclosed in U.S. Pat. No. 4,473,295, issued Sept. 25, 1984. The apparatus of that patent employs a pair of parabolic mirrors having a common focal point, and positioned so that collimated radiation collected by the first mirror is brought to a focus on a reflecting surface; and, after reflection, is collected by the second mirror and recollimated along its original path.

In FIG. 3, the sample-carrying substrate 28 has the samples on its upper, or front, surface 42 (note the upside-down reversal from FIG. 2), and has a reflecting layer 44 on its lower, or back, surface. The substrate, which must be transparent to infrared radiation, may be fabricated from a material such as zinc selenide. The reflecting surface 44 is preferably deposited on the rear of the substrate; but reflection could also be obtained by using a separate mirror behind the substrate. In either case, both the substrate and the reflecting surface may be fastened directly to a cooled plate 46.

Collimated IR radiation 48 from an FTIR spectrometer is incident on a parabolic mirror 50 from the left. This mirror brings the radiation to a focus 52 at the deposited sample 54 on the front surface 42 of the substrate. After passing through the sample, and being partially absorbed, the IR radiation is reflected by the reflecting surface 44 toward a second parabolic mirror 56. This mirror has been displaced from the position normally used in the two mirror sampler toward the substrate surface a distance 2y, where y is the optical path length between the front surface of the substrate and the reflecting back surface. (This optical path length is equal to the thickness of the substrate times its index of refraction). The focal point of mirror 56 thus falls at position 58, which is the mirror image of focal point 52, as formed by reflecting surface 44. The radiation collected by mirror 56 will thus emerge collimated and on a path parallel to, but laterlly displaced from, its input path.

The apparatus in FIG. 3 provides a simple, reliable means for measuring the IR absorption of the deposited sample 54, while discriminating against radiation reflected from the surface of the sample. Although some of this spurious reflected radiation will strike mirror 56, it will be far out of focus, and thus will not be collimated by mirror 56. In fact, any chance of spurious reflected radiation reaching the detection system can be eliminated by removing a small portion of either mirror close to the vertical axis (note dashed lines 60). It should be noted that the apparatus in FIG. 3 is symmetrical, in the sense that the sample could just as well be illuminated from the back by using mirror 56 to focus the input radiation at 52 (after reflection from 44), and mirror 50 to collect the radiation after sample illumination.

Another embodiment of the invention has been designed to be incorporated into an infrared microscope similar to the apparatus disclosed in common-assignee U.S. patent application (Ser. Nos. 907,993, filed Sept. 16, 1986, 907,995 filed Sept. 16, 1986, and 921,066, filed Oct. 20, 1986), the disclosures of which are incorporated herein by reference, in order to provide more detailed information. Before the microscope structure is discussed, the principles of the invention will be explained, using a simplified illustration.

Figure 4:
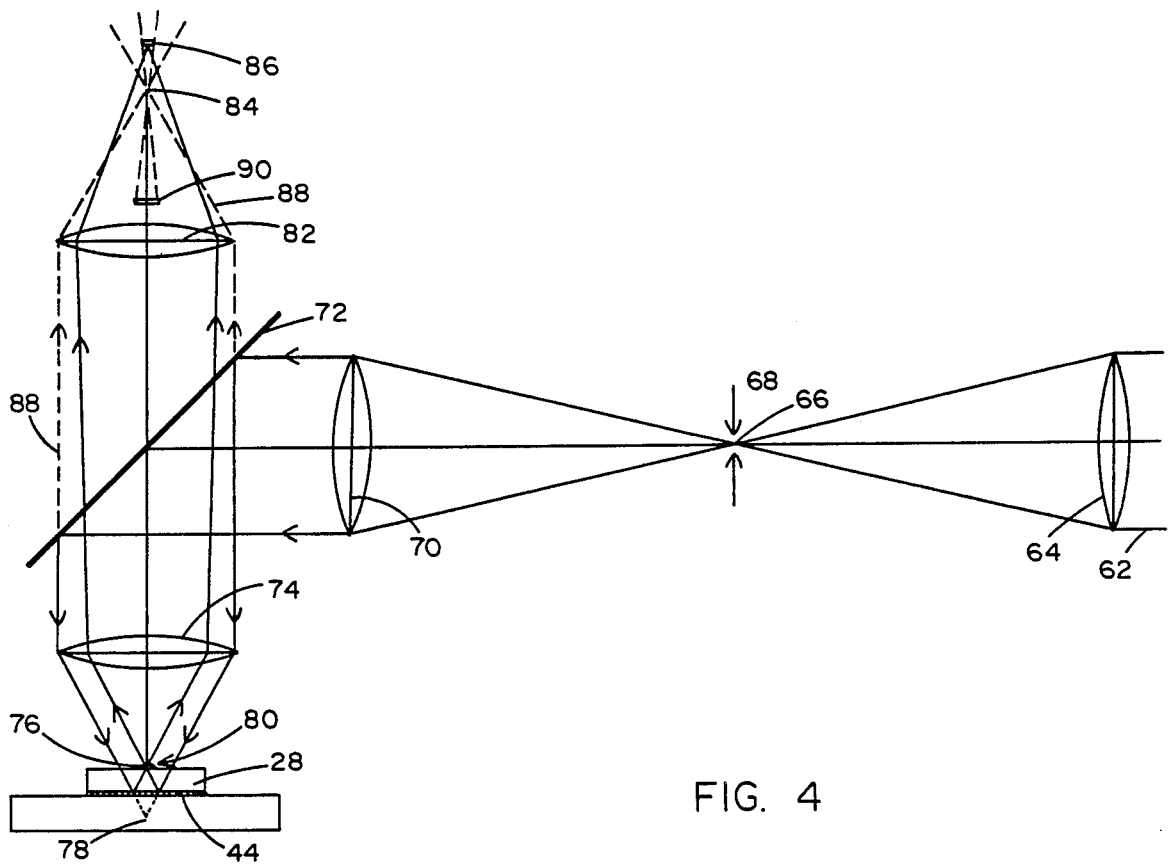
FIG. 4 is a schematic showing of an optical system, used to explain the principles involved in a second embodiment of the invention.

In FIG. 4, nominally collimated input radiation 62 is brought to a focus by lens 64, at a focal point 66. A field stop 68 is used to define the total field to be illuminated at the sample. The radiation passing through field stop 68 is recollimated by a lens 70, and then partially reflected by a beamsplitter 72 (nominally 50% reflecting) toward a lens 74. Lens 74 brings the radiation to a focus at 76 (after transmission through substrate 28, and reflection by reflecting layer 44). Point 78 indicates the position of the reflected image of focal point 76. The area illuminated at 76 is determined by the open area of field stop 68, and the ratio of the focal lengths of lens 70 and lens 74.

For simplicity, assume that field stop 68 and focal point 76 are in the focal planes of lens 70 and lens 74, respectively (after reflection, in the case of point 76). The radiation traveling between lens 70 and lens 74 will thus be nominally collimated. After passing the region of focal point 76, and any sample 80 located in this region, the radiation will diverge and again strike lens 74. However, since no reflection is involved in this portion of the path, lens 74 will see the radiation as coming from a point inside of its focal point. The radiation will continue to diverge somewhat after passing through lens 74 and will travel to a lens 82. The focal point of lens 82 is indicated as 84. The radiation transmitted by the sample 80 will be imaged at a point behind 84, indicated by the location of a detector 86.

Any radiation reflected from the surface of sample 80 will retrace the path of the incident radiation and will be recollimated by lens 74. A portion of this (indicated by dashed lines 88) will pass through the beamsplitter 72 and will be imaged by lens 82 in its focal plane 84. After passing through 84, this radiation will diverge, so as to be substantially out of focus by the time it reaches the infrared detector 86. Thus very little of this spurious radiation will be detected. Detection of the spurious radiation can be completely eliminated by placing a blocking stop at a position such as that indicated by 90, where it will form a shadow on the detector 86.

Figure 5:
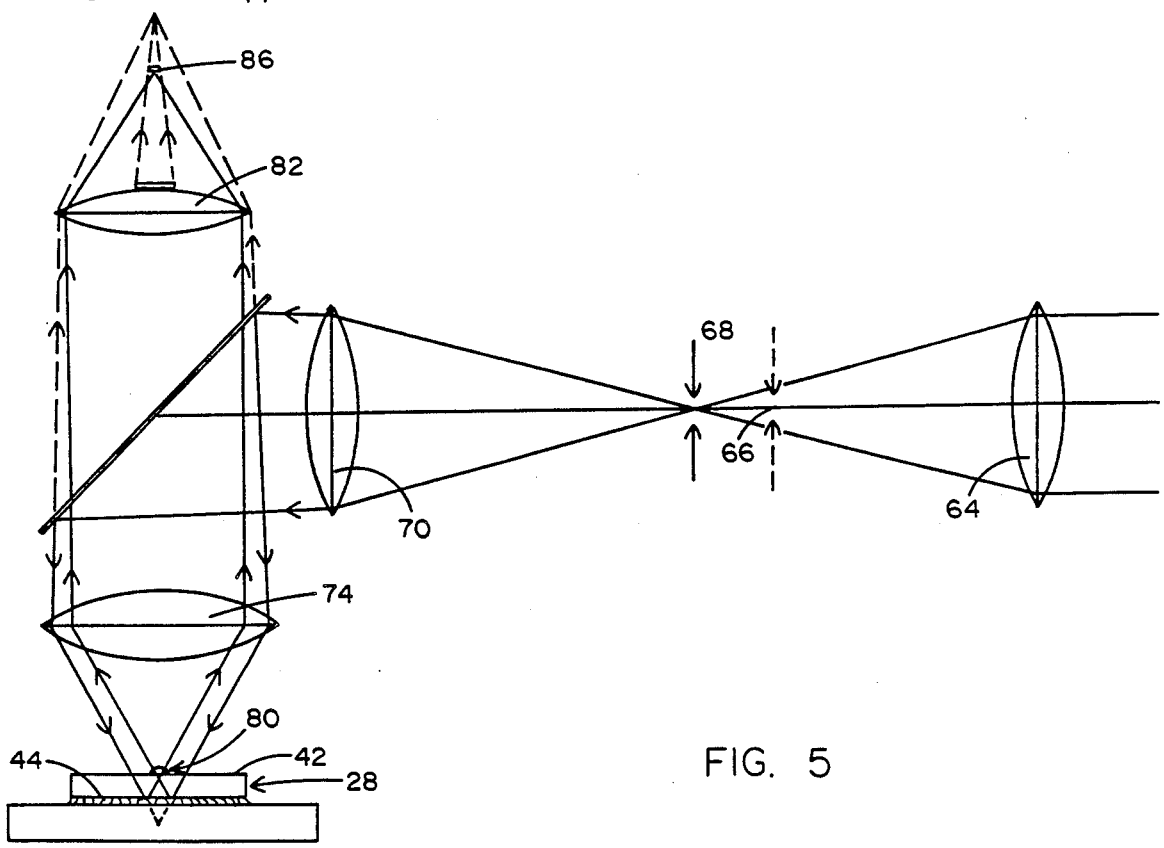
FIG. 5 is a schematic showing a revised version of the optical system of FIG. 4.

In FIG. 4, the input radiation was first collimated and then brought to a focus at the sample; and the detector was then displaced from its normal position to compensate for the defocusing of the collection optics. FIG. 5 illustrates a slightly different configuration, which turns out to be more convenient for use with practical infrared optics. Here the detector 86 is placed at the focal point of lens 82, so that the detected radiation is nominally collimated between lens 74 and lens 82. The surface 42 of the substrate 28 is then positioned so that the sample 80 is in the focal plane of lens 74, and thus is imaged directly on the detector 86. In order to image the incident radiation on the sample after reflection from surface 44, it is necessary to defocus lens 70, so as to compensate for the fact that the sample is no longer in the focal plane of the incident radiation. This is done by displacing field stop 68 from the position of the focal point 66 of lens 70. Lens 64 can be displaced to the left, if desired, so as to concentrate the input radiation at field stop 68. However, this will often not be necessary, since in most practical situations the incident radiation will have greater divergence than the system can handle. It should be noted that in the example given in FIG. 5, the incident radiation is not collimated between lens 70 and lens 74.

Figure 6:
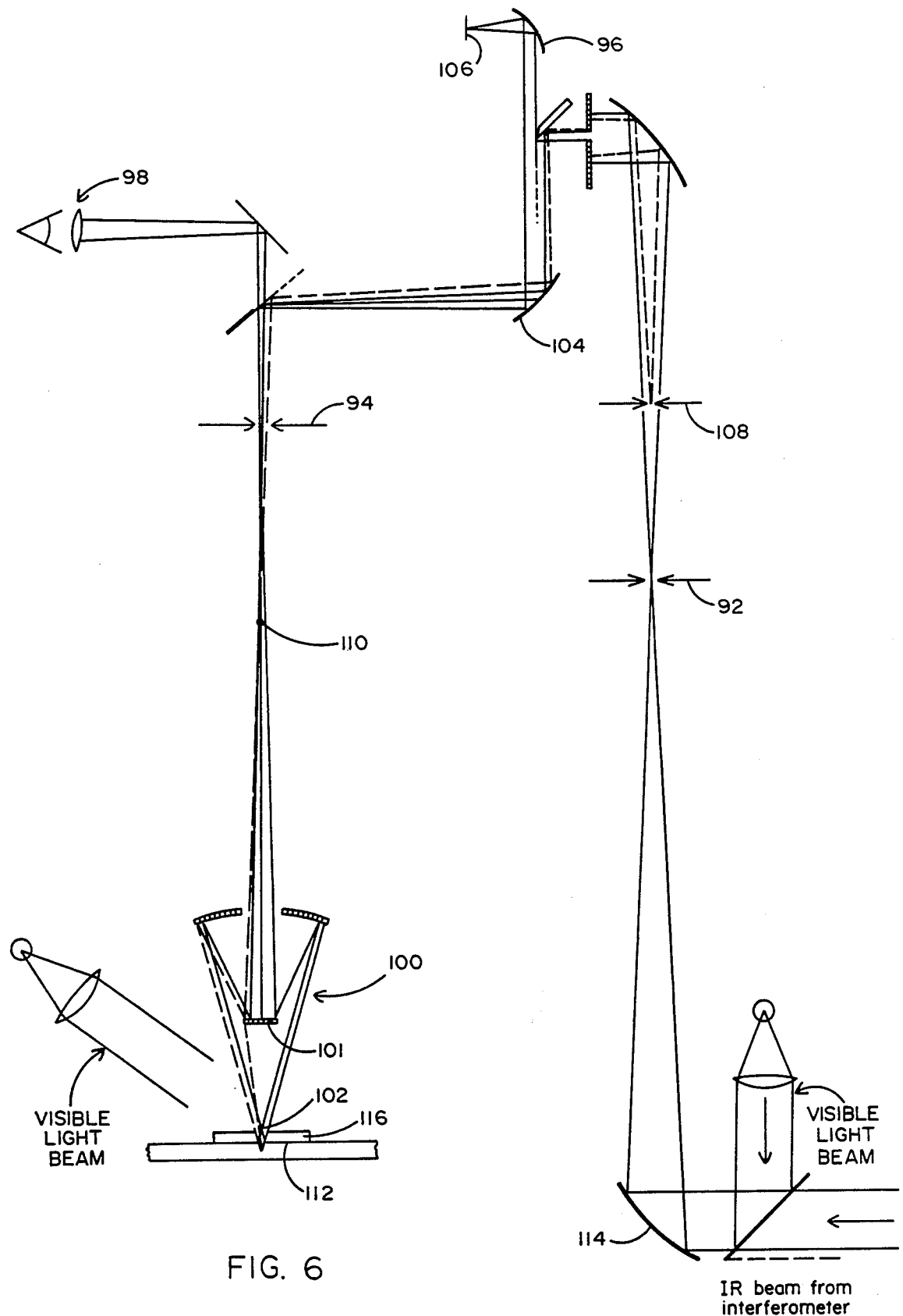
FIG. 6 is a schematic showing the optical system of a practical embodiment of the present invention based on the commercial IR microscope disclosed in application Ser. Nos. 907,993 and 907,995, both filed Sept. 16, 1986.

A practical embodiment of the present invention adapted for a commercial IR microscope is shown in FIG. 6. As stated above, various aspects of this microscope have been disclosed in previous patent application Ser. Nos. 907,993, 907,995 and 921,066, LPC-7 being of particular interest in explaining the structure of FIG. 6. In that application, an adjustable field stop 92 (not the same numeral as in LPC-7) is used to define the area of the sample to be illuminated, without needing to close the normal viewing field stop 94. This capability proves to be quite useful in allowing the practical construction of a gas chromatograph infrared (GC/IR) analysis system along the lines outlined with reference to FIG. 5. In this case, the detector remains in its normal position in the focal plane of mirror 96. This is important, since mirror 96 is a short focal-length, off-axis paraboloid. This type of mirror has severe abberations, except in the immediate vicinity of its focal point.

An eyepiece 98 in the microscope can be used visually to place the sample region on axis, in the focal plane of a Cassegrain objective lens 100, in which case the sample at 102 will form an enlarged image in the plane of field stop 94. The radiation from the center of the sample will be collimated by a mirror 104, and then focused on the center of detector 106 by mirror 96.

For the present purpose, field stop 92 is moved to a new position 108, chosen so as to give rise to an image at 110, and eventually a greatly reduced image at the sample 102, after reflection from reflecting surface 112. The value of the projected field stop 92/108 for the present invention resides in the fact that the incident beam no longer is imaged in the plane of field stop 94, making it necessary to leave this field stop open. It will generally not be necessary to move mirror 114 to compensate for the displacement of field stop 92/108, due to the fact that the incident beams, both IR analysis and visible alignment beams, will both have sufficient divergence to flood the aperture with radiation, even though it is not at the focus of mirror 114.

Another convenient feature of this design is the fact that the small secondary mirror 101 in the Cassegrain acts as an aperture stop, effectively creating a hole in the center of the Cassegrain's field of view. As long as the thickness of sample-carrying substrate 116 is large compared to the dimensions of the sample, this hole will shade the detector channel from spurious radiation reflected from the surface of the sample.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. An optical apparatus for spectral analysis of samples in the transmission mode, comprising:
   a transparent substrate having a front sample-supporting surface;
   a radiation source which supplies sample-illuminating radiation;
   means for focusing sample-illuminating radiation at the sample, said means being positioned in front of the sample;
   a reflecting surface at the back of the substrate which reflects the sample-illuminating radiation either before or after it passes through the sample;
   means for collecting such reflected radiation after it has passed through the sample, said means being positioned in front of the sample; and
   a detector which receives the radiation after illumination of the sample;
   the radiation path from the radiation source through the sample to the detector being so directed that an image of the sample is formed at the detector by radiation which has been focused at the sample once and only once and has been reflected at the back of the substrate once and only once, in order to minimize the sample-reflected radiation which reaches the detector.

2. The apparatus of claim 1 in which the radiation is reflected by the reflecting surface before it is focussed at the sample.

3. The apparatus of claim 1 in which the radiation is reflected by the reflecting surface after it is focussed at the sample.

4. The apparatus of claim 1 which also comprises:
   an adjustable field stop which defines the area of the sample to be illuminated, and which is so located as to be imaged at the mirror image of the sample.

5. The apparatus of claim 1 in which the means for directing and means for collecting radiation comprise:
   a first parabolic mirror having its focal point at the sample; and
   a second parabolic mirror having its focal point at the mirror image of the sample.

6. The apparatus of claim 1 in which the means for directing and means for collecting radiation comprise:
   a first parabolic mirror which directs radiation toward the sample; and
   a second parabolic mirror which collects radiation after it has passed through the sample;
   the focal points of the first and second parabolic mirrors being displaced by a distance equal to approximately twice the optical path length between the front surface and the reflecting back surface of the substrate.

7. The apparatus of claim 1 which also comprises:

a cooling element against one surface of which the rear of the substrate is mounted.

8. An optical apparatus, for spectral analysis of chromatographically separated samples in the transmission mode, comprising:
  a detector which measures sample-altered infrared radiation;
  an infrared transparent substrate having a front sample-supporting surface;
  an infrared reflecting surface at the back of the substrate;
  means for causing pre-sample infrared radiation to travel from the source and to be focused at and transmitted through the sample, a portion of such pre-sample radiation being reflected by the sample; and
  means for causing sample-transmitted radiation to be reflected by the reflecting surface and then be focused at the detector, and for causing sample-reflected radiation not to be focused at the detector.

9. The optical apparatus of claim 8 which comprises:
  means for imaging the sample on the detector by radiation which is reflected by the reflecting surface after it passes through the sample.

10. An optical apparatus, for spectral analysis of chromatographically separated samples in the transmission mode, comprising:
  a source of infrared radiation;
  a detector which measures sample-altered infrared radiation;
  an infrared transparent substrate having a front sample-supporting surface;
  an infrared reflecting surface at the back of the substrate;
  means for causing pre-sample infrared radiation to travel from the source, to be reflected by the reflecting surface, and then to be focused at and transmitted through the sample; and
  means for causing post-sample radiation to be focused at the detector.

11. The optical apparatus of claim 10 which comprises:
  means for imaging the sample on the detector by radiation which is reflected by the reflecting surface before it passes through the sample.

* * * * *